(12) United States Patent
Huang et al.

(10) Patent No.: US 10,605,790 B2
(45) Date of Patent: Mar. 31, 2020

(54) DEVICE AND METHOD FOR DETECTING DEFECT IN MAIN SHAFT OF WIND TURBINE

(71) Applicant: Tsinghua University, Beijing (CN)

(72) Inventors: Songling Huang, Beijing (CN); Wei Zhao, Beijing (CN); Yu Zhang, Beijing (CN); Qing Wang, Beijing (CN); Shen Wang, Beijing (CN)

(73) Assignee: TSINGHUA UNIVERSITY, Beijing (CN)

( * ) Notice: Subject to any disclaimer, the term of this patent is extended or adjusted under 35 U.S.C. 154(b) by 168 days.

(21) Appl. No.: 15/665,535

(22) Filed: Aug. 1, 2017

(65) Prior Publication Data

US 2018/0038835 A1     Feb. 8, 2018

(30) Foreign Application Priority Data

Aug. 8, 2016    (CN) .......................... 2016 1 0645817

(51) Int. Cl.
     *G01N 29/44*      (2006.01)
     *G01N 29/24*      (2006.01)
     (Continued)

(52) U.S. Cl.
     CPC ............. *G01N 29/44* (2013.01); *F03D 17/00* (2016.05); *F03D 80/50* (2016.05); *G01N 29/04* (2013.01);
     (Continued)

(58) Field of Classification Search
     CPC ......... F03D 17/00; G01N 29/34; G01N 29/26
     (Continued)

(56) References Cited

U.S. PATENT DOCUMENTS

| | | | | |
|---|---|---|---|---|
| 3,500,368 A | * | 3/1970 | Abe ........................ | G01T 7/125 250/382 |
| 6,399,948 B1 | * | 6/2002 | Thomas ................. | G01N 25/72 250/334 |

(Continued)

FOREIGN PATENT DOCUMENTS

| | | | | |
|---|---|---|---|---|
| CN | 101813670 | | 8/2010 | |
| CN | 202230061 | * | 5/2012 | ............. G01N 29/07 |

(Continued)

OTHER PUBLICATIONS

SIPO, First Office Action for CN Application No. 201610645817, dated Jun. 29, 2018.

(Continued)

*Primary Examiner* — Jacques M Saint Surin
(74) *Attorney, Agent, or Firm* — Hodgson Russ LLP

(57) ABSTRACT

The present disclosure provides a device and method for detecting a defect in a main shaft of a wind turbine. The device includes: an excitation source, configured to generate an electromagnetic ultrasonic guided wave signal; a nickel strap, magnetized and disposed on an outer surface of an end of the main shaft; a coil, disposed at the nickel strap, configured to receive the electromagnetic ultrasonic guided wave signal such that the electromagnetic ultrasonic guided wave signal propagates in the main shaft, the coil and the nickel strap being configured to transform the electromagnetic ultrasonic guided wave signal propagating in the main shaft into an electrical signal by electromagnetic induction; a signal collector, configured to collect the electrical signal and transform the electrical signal into guided wave detection data and a wireless communication component, configured to transmit the guided wave detection data to a remote equipment.

17 Claims, 3 Drawing Sheets

(51) Int. Cl.

| | | |
|---|---|---|
| *G01N 29/07* | (2006.01) | |
| *G01N 29/12* | (2006.01) | |
| *F03D 17/00* | (2016.01) | |
| *F03D 80/50* | (2016.01) | |
| *G01N 29/04* | (2006.01) | |
| *G01N 29/22* | (2006.01) | |
| *G01N 29/26* | (2006.01) | |
| *G01N 29/34* | (2006.01) | |

(52) U.S. Cl.
CPC ............ *G01N 29/07* (2013.01); *G01N 29/12* (2013.01); *G01N 29/221* (2013.01); *G01N 29/2412* (2013.01); *G01N 29/2481* (2013.01); *G01N 29/26* (2013.01); *G01N 29/34* (2013.01); *F05B 2240/60* (2013.01); *F05B 2260/83* (2013.01); *G01N 2291/0425* (2013.01); *G01N 2291/2634* (2013.01); *G01N 2291/2693* (2013.01)

(58) Field of Classification Search
USPC .......................................................... 73/584
See application file for complete search history.

(56) References Cited

U.S. PATENT DOCUMENTS

| | | | |
|---|---|---|---|
| 2012/0092020 A1* | 4/2012 | Zhou ................. | G01R 31/1209 324/537 |
| 2014/0191767 A1* | 7/2014 | Zhou ..................... | G01R 31/04 324/538 |

FOREIGN PATENT DOCUMENTS

| | | | |
|---|---|---|---|
| CN | 202330358 | * 7/2012 | ............. G01N 27/82 |
| CN | 102662003 | 9/2012 | |
| CN | 202562456 | 11/2012 | |
| CN | 202789321 | 3/2013 | |
| CN | 202994735 | 6/2013 | |
| CN | 103412049 | 11/2013 | |
| CN | 104198594 | * 12/2014 | |
| JP | 360105960 | * 6/1985 | |
| WO | 2015065873 | 5/2015 | |

OTHER PUBLICATIONS

Wei et al., "Magnetostriction-Based Omni-Directional Guided Wave Transducer for High-Accuracy Tomography of Steel Plate Defects," IEEE Sensors Journal, vol. 15, No. 11, Nov. 2015, pp. 6549-6558.
Huang et al., "Electromagnetic Ultrasonic Guided Waves," Springer Series in Measurement Science and Technology, ISSN 2198-7807, ISBN 978-981-10-0562-6, 2016.
Huang et al., "Theory and Application of Electromagnetic Ultrasonic Guided Wave," E & E, 2013, pp. 11-21.
Cho et al., "Noncontact torsional wave transduction in a rotating shaft using oblique magnetostrictive strips," Journal of Applied Physics, American Institute of Physics, 2006, 100, 104903-1-6.
SIPO, Second Office Action for CN Application No. 201610645817.3, dated Feb. 3, 2019.

* cited by examiner

DEVICE AND METHOD FOR DETECTING DEFECT IN MAIN SHAFT OF WIND TURBINE

CROSS-REFERENCE TO RELATED APPLICATION

This application claims priority to and benefits of Chinese Patent Application No. 201610645817.3, filed with the State Intellectual Property Office of P. R. China on Aug. 8, 2016, the entire contents of which are incorporated herein by reference.

FIELD

The present disclosure relates to the nondestructive testing technology field, and more particularly, to a device for detecting a defect in a main shaft of a wind turbine and a method for detecting a defect in a main shaft of a wind turbine.

BACKGROUND

A main shaft is a key component of a wind turbine, which connects a rotator with a gearbox for passing energy. However, complex force and wear inevitably lead to cracks and other defects in the main shaft during a long operation process. For the normal operation of the main shaft and wind turbine, it is important to find the defects.

However, the wind turbine is far away from the ground, typically, the wind turbine is established on an ocean platform, which is far away from the land (few kilometers to tens of kilometers), thus it is difficult to detect the defects in the main shaft of the wind turbine in real time.

In the related art, in order to detect the defects in a main shaft of the wind turbine, it is necessary to shut down the wind turbine and the inspector needs to enter into a wind turbine monitor room to detect the main shaft, which may lead to financial loss, and a waste of manpower, material and financial resources.

Moreover, during the operation process of the wind turbine, the main shaft rotates in circumferential direction, and the rotate speed varies continually. If the main shaft is detected after the wind turbine is shut down, it is difficult to monitor the operation conditions of the main shaft, such that it is inconvenient to know the actual condition of the main shaft.

SUMMARY

Embodiments of the present disclosure provide a device for detecting a defect in a main shaft of a wind turbine. The device includes: an excitation source, configured to generate an electromagnetic ultrasonic guided wave signal; a nickel strap, magnetized and disposed on an outer surface of an end of the main shaft circumferentially; a coil, disposed at the nickel strap correspondingly, and configured to receive the electromagnetic ultrasonic guided wave signal such that the electromagnetic ultrasonic guided wave signal propagates in the main shaft, in which the coil and the nickel strap are configured to transform the electromagnetic ultrasonic guided wave signal propagating in the main shaft into an electrical signal by electromagnetic induction; a signal collector, configured to collect the electrical signal and transform the electrical signal into guided wave detection data; and a wireless communication component, configured to transmit the guided wave detection data to a remote equipment, such that the defect is determined according to the guided wave detection data at the remote equipment.

Embodiments of the present disclosure provide a method for detecting a defect in a main shaft of a wind turbine. A nickel strap is magnetized and disposed on an outer surface of an end of the main shaft, and a coil is disposed at the nickel strap correspondingly. The method includes: generating an electromagnetic ultrasonic guided wave signal; receiving, by the coil, the electromagnetic ultrasonic guided wave signal, such that the electromagnetic ultrasonic guided wave signal propagates in the main shaft; transforming, by the coil and the nickel strap, the electromagnetic ultrasonic guided wave signal propagating in the main shaft into an electrical signal; transforming the electrical signal into guided wave detection data; and transmitting the guided wave detection data to a remote equipment, such that the defect is determined according to the guided wave detection data at the remote equipment.

Embodiments of the present disclosure provide a method for manufacturing a device for detecting a defect in a main shaft of a wind turbine. The method includes: determining an electromagnetic ultrasonic guided wave signal to be generated by an excitation source installed in the device; drawing a dispersion curve of the electromagnetic ultrasonic guided wave signal according to an outer diameter, an inner diameter and material characteristic of the main shaft; selecting an operating point of the electromagnetic ultrasonic guided wave signal and determining an operating frequency and a wave speed of the electromagnetic ultrasonic guided wave signal according to the dispersion curve; calculating a width, a length, and a thickness of a nickel strap to be used in the device according to the operating frequency and the wave speed; determining a number of turns, a width and a cross sectional area of a coil to be used in the device, and a radial distance between the coil and the nickel strap; magnetizing the nickel strap by sliding a permanent magnet uniformly along a longitudinal direction of the nickel strap, such that a residual magnetic field in the longitudinal direction is generated in the nickel strap; painting epoxy resin glue on an inner surface of the nickel strap; sticking the nickel strap magnetized on to an outer surface of an end of the main shaft circumferentially; installing the coil on an outer side of the nickel strap magnetized to enable a center of the coil to coincide with a center of the nickel strap magnetized and to enable the coil to distance from nickel strap magnetized the radial distance; and and installing the signal collector and the wireless communication component in the device.

It is to be understood that both the foregoing general description and the following detailed description are exemplary and explanatory only and are not restrictive of the invention, as claimed.

BRIEF DESCRIPTION OF THE DRAWINGS

In order to explicitly illustrate embodiments of the present disclosure, a brief introduction for the accompanying drawings corresponding to the embodiments will be listed as follows. Apparently, the drawings described below are only corresponding to some embodiments of the present disclosure, and those skilled in the art may obtain other drawings according to these drawings without creative labor.

DETAILED DESCRIPTION

Figure 1:
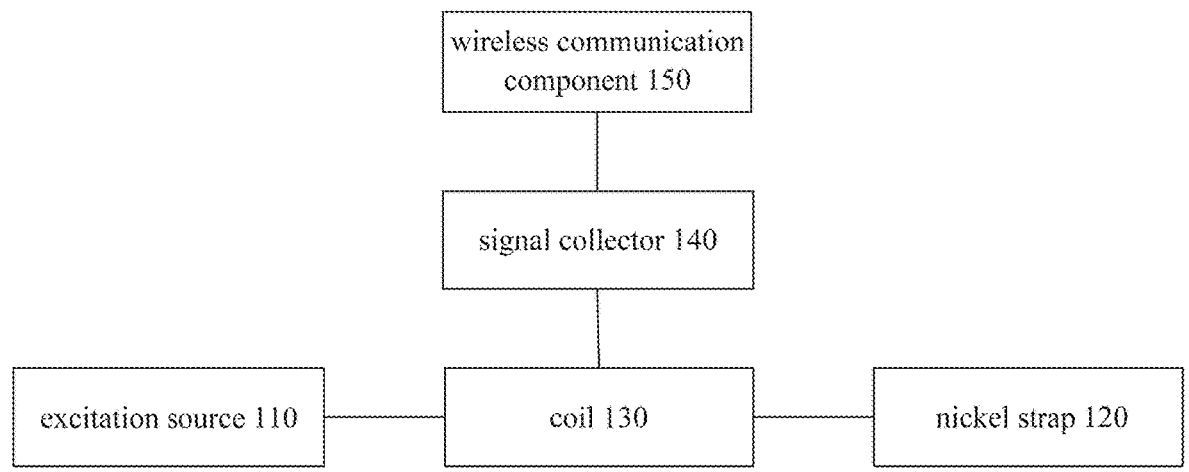
FIG. 1 is a block diagram of a device for detecting a defect in a main shaft of a wind turbine according to an exemplary embodiment.

Reference will be made in detail to embodiments of the present disclosure. The same or similar elements and the elements having same or similar functions are denoted by like reference numerals throughout the descriptions. The embodiments described herein with reference to drawings are explanatory, illustrative, and used to generally understand the present disclosure. The embodiments shall not be construed to limit the present disclosure.

In the specification, unless specified or limited otherwise, relative terms such as "central", "longitudinal", "lateral", "front", "rear", "right", "left", "inner", "outer", "lower", "upper", "horizontal", "vertical", "above", "below", "up", "top", "bottom" as well as derivative thereof (e.g., "horizontally", "downwardly", "upwardly", etc.) should be construed to refer to the orientation as then described or as shown in the drawings under discussion. These relative terms are for convenience of description and do not require that the present disclosure be constructed or operated in a particular orientation.

In the description of the present disclosure, it should be understood that, unless specified or limited otherwise, the terms "mounted," "connected," and "coupled" and variations thereof are used broadly and encompass such as mechanical or electrical mountings, connections and couplings, also can be inner mountings, connections and couplings of two components, and further can be direct and indirect mountings, connections, and couplings, which can be understood by those skilled in the art according to the detail embodiment of the present disclosure.

Referring to the following descriptions and drawings, these and other aspects of the embodiments of the present disclosure will be apparent. In these descriptions and drawings, some specific embodiments of the present disclosure are provided, so as to show some ways to implement the principle of the embodiments of the present disclosure. However it should be understood that the embodiment of the present disclosure is not limited thereby. Instead, the embodiments of the present disclosure comprise all the variants, modifications and their equivalents within the spirit and scope of the present disclosure as defined by the claims.

A device for detecting a defect in a main shaft of a wind turbine and a method for detecting a defect in a main shaft of a wind turbine according to embodiments of the present disclosure will be described in the following with reference to the drawings.

Figure 2:
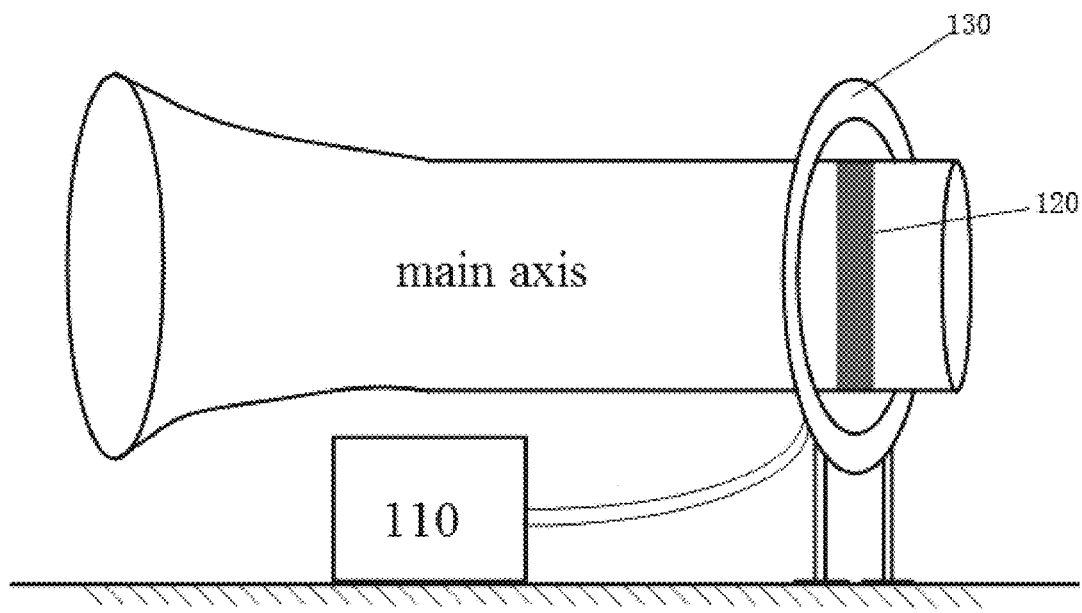
FIG. 2 is a schematic diagram of a mounting of a coil and a nickel strap according to an exemplary embodiment.

FIG. 1 is a block diagram of a device for detecting a defect in a main shaft of a wind turbine according to an exemplary embodiment. FIG. 2 is a schematic diagram of a mounting of a coil and a nickel strap according to an exemplary embodiment. As illustrated in FIG. 1 and FIG. 2, the device includes an excitation source 110, a nickel strap 120, a coil 130, a signal collector 140 and a wireless communication component 150.

The excitation source 110 is configured to generate an electromagnetic ultrasonic guided wave signal. The excitation source 110 is further configured to transmit the generated electromagnetic ultrasonic guided wave signal to the coil 130.

In at least one embodiment of the present disclosure, the electromagnetic ultrasonic guided wave signal is a periodic pulse square wave signal. The excitation source 110 is configured to convert direct current (DC for short) voltage to the periodic pulse square wave signal through a full-bridge inverter.

In at least one embodiment of the present disclosure, the electromagnetic ultrasonic guided wave signal has a T-mode, which is uniform circumferentially and propagates along an axial direction.

The nickel strap 120 is magnetized and disposed on an outer surface of an end of the main shaft. The coil 130 is disposed at the nickel strap 120 correspondingly. The arrangement of the coil 130 and the nickel strap 120 is illustrated in FIG. 2. That is, the nickel strap 120 and the coil 130 are disposed on the outer surface of the end of the main shaft circumferentially.

The coil 130 is configured to receive the electromagnetic ultrasonic guided wave signal such that the electromagnetic ultrasonic guided wave signal propagates in the main shaft. The coil 130 and the nickel strap 120 are configured to transform the electromagnetic ultrasonic guided wave signal propagating in the main shaft into an electrical signal by electromagnetic induction.

The signal collector 140 is configured to collect the electrical signal and transform the electrical signal into guided wave detection data. The wireless communication component 150 is configured to transmit the guided wave detection data to a remote equipment, such that the defect is determined according to the guided wave detection data at the remote equipment.

Figure 3:
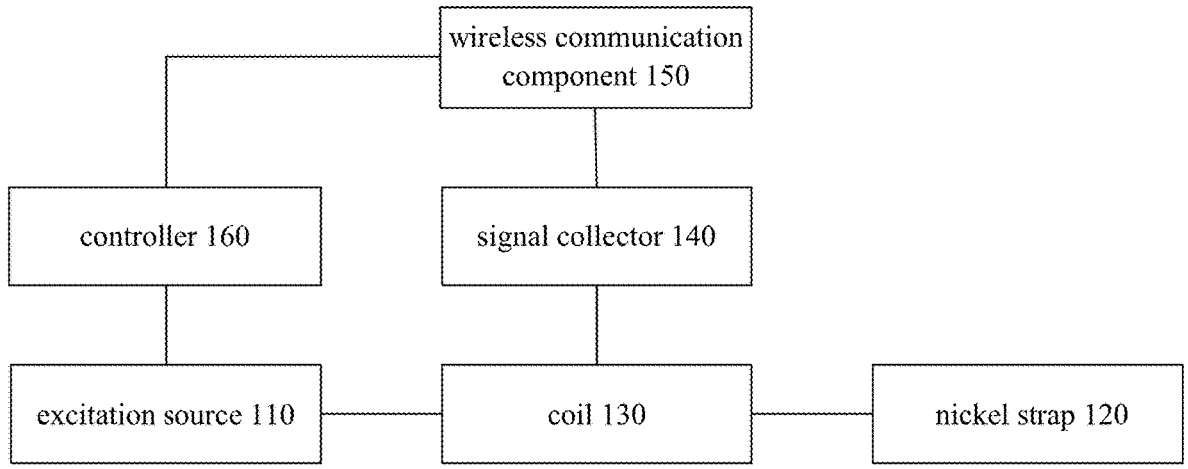
FIG. 3 is a block diagram of a device for detecting a defect in a main shaft of a wind turbine according to an exemplary embodiment.

In at least one embodiment of the present disclosure, the device further includes a controller. As illustrated in FIG. 3, the controller 160 is configured to control the excitation source 110 to generate the electromagnetic ultrasonic guided wave signal. In at least one embodiment of the present disclosure, the controller 160 may be a Field Programmable Gate Array (FPGA) chip. In at least one embodiment of the present disclosure, the device further includes a storage. The storage is configured to receive and store the guided wave detection data. In at least one embodiment of the present disclosure, the storage may be a solid-state hard disk. The storage is connected with the wireless communication component 150. The controller 160 is further configured to control the wireless communication component 150 to transmit the guided wave detection data to the remote equipment regularly.

In at least one embodiment of the present disclosure, the wireless communication component 150 is implemented by a wireless bridge. The guided wave detection data stored in the solid-state hard disk is transferred to a TCP/IP (Transmission Control Protocol/Internet Protocol) conversion module under a control of the controller 160. That is, the original data is converted into network standard data. The transmitting bridge transmits the network standard data and the receiving bridge receives the network standard data. The received network standard data is converted by the TCP/IP conversion module. The converted data is transmitted to processing software in the remote equipment for processing and analysis. For example, a ZX-2415H 802.11b bridge is employed, which operates at a 2.4 GHz frequency band, meets IEEE 802.11b standard, and adopts Direct Sequence Spread Spectrum (DSSS) technology, thereby having a high transmission rate, a high reception sensitivity, a far transmission distance and other characteristics. Its actual transmission rate may be up to 6 Mbps. In addition, the ZX-2415H 802.11b bridge has a waterproof function and is suitable for conditions of the wind turbine and data wireless transmission.

In at least one embodiment of the present disclosure, a length of the nickel strap 120 is less than a circumference of the outer surface of the end of the main shaft by a preset value. That is, a gap may be formed between two poles of the nickel strap 120, thereby providing a bias magnetic field in a circumferential direction of the main shaft.

In at least one embodiment of the present disclosure, the device further includes a matching and coupling component. The matching and coupling component is configured to receive the electromagnetic ultrasonic guided wave signal, and match and couple the electromagnetic ultrasonic guided wave signal, and transmit the electromagnetic ultrasonic guided wave signal after matching and coupling to the coil 130. In at least one embodiment of the present disclosure, the matching and coupling component is further configured to receive the electrical signal, and match and couple the electrical signal, and transmit the electrical signal after matching and coupling to the signal collector 140.

In at least one embodiment of the present disclosure, the nickel strap 120 is magnetized in such a manner that a permanent magnet slides uniformly along a longitudinal direction of the nickel strap 120 such that a residual magnetic field in the longitudinal direction is generated in the nickel strap 120.

In at least one embodiment of the present disclosure, a center of the coil 130 coincides with a center of the nickel strap 120.

In at least one embodiment of the present disclosure, an inner surface of the nickel strap 120 is painted with epoxy resin glue.

With the device for detecting a defect in a main shaft of a wind turbine according to embodiments of the present disclosure, it is easy to monitor the conditions of the main shaft in real time, thus avoiding the waste of manpower, material and financial resources due to the shutdown of the wind turbine. The device for detecting a defect in a main shaft of a wind turbine has a wide application prospect.

Embodiments of the present disclosure further provide a method for detecting a defect in a main shaft of a wind turbine. A nickel strap is magnetized and disposed on an outer surface of an end of the main shaft, and a coil is disposed at the nickel strap correspondingly.

Figure 4:
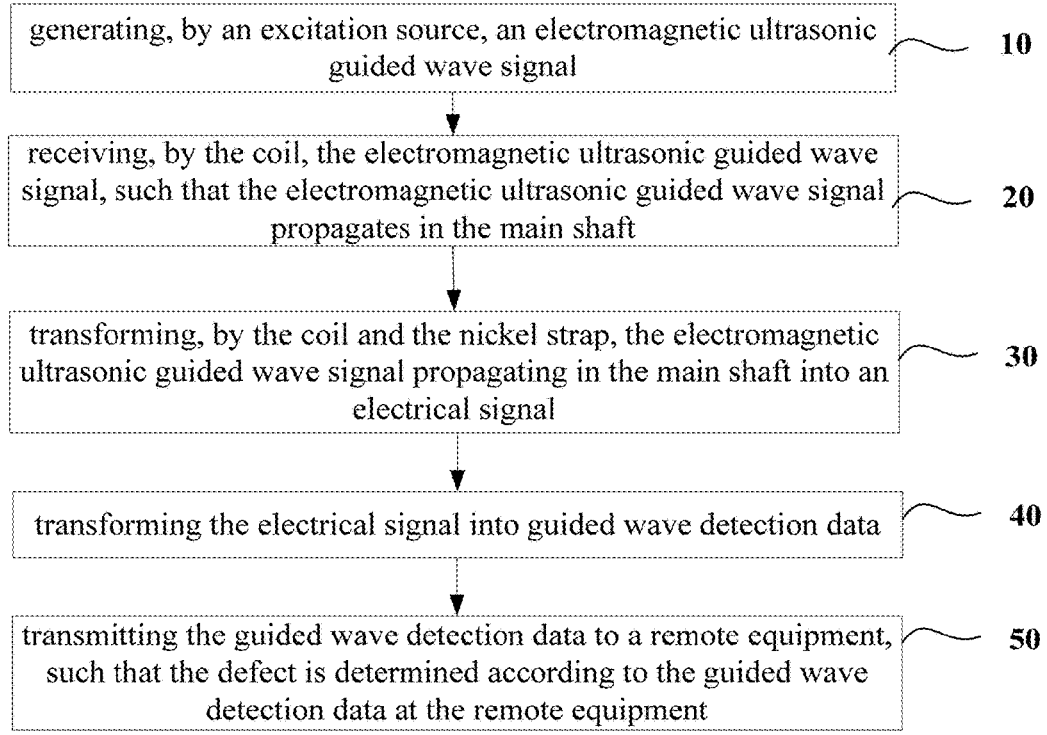
FIG. 4 is a flow chart of a method for detecting a defect in a main shaft of a wind turbine according to an exemplary embodiment.

FIG. 4 is a flow chart of a method for detecting a defect in a main shaft of a wind turbine according to an exemplary embodiment. As illustrated in FIG. 4, the method includes followings.

At block 10, an excitation source generates an electromagnetic ultrasonic guided wave signal.

At block 20, the coil receives the electromagnetic ultrasonic guided wave signal, such that the electromagnetic ultrasonic guided wave signal propagates in the main shaft.

A block 30, the coil and the nickel strap transform the electromagnetic ultrasonic guided wave signal propagating in the main shaft into an electrical signal.

A block 40, the electrical signal is transformed into guided wave detection data.

A block 50, the guided wave detection data is transmitted to a remote equipment, such that the defect is determined according to the guided wave detection data at the remote equipment.

In at least one embodiment of the present disclosure, the electromagnetic ultrasonic guided wave signal is a periodic pulse square wave signal.

In at least one embodiment of the present disclosure, the electromagnetic ultrasonic guided wave signal has a T-mode, which is uniform circumferentially and propagates along an axial direction.

Figure 5:
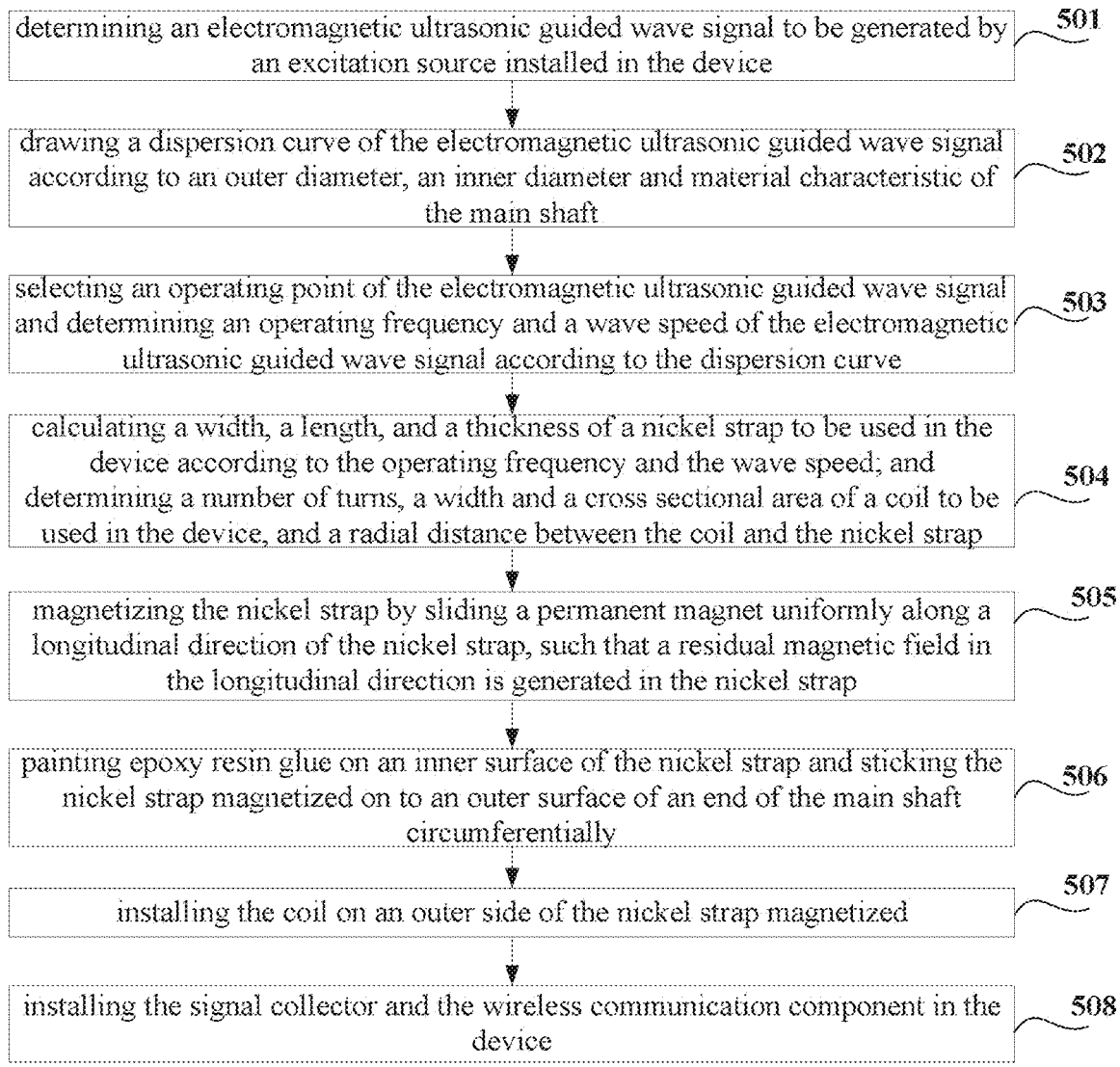
FIG. 5 is a flow chart showing a method for manufacturing the device for detecting a defect in a main shaft of a wind turbine according to an embodiment of the present disclosure.

Embodiments of the present disclosure further provide a method for manufacturing the device for detecting a defect in a main shaft of a wind turbine. FIG. 5 is a flow chart showing a method for manufacturing the device for detecting a defect in a main shaft of a wind turbine according to an embodiment of the present disclosure. As shown in FIG. 5, the method includes the followings.

At act 501, an electromagnetic ultrasonic guided wave signal to be generated by an excitation source installed in the device is determined.

Generally, a T-mode guided wave signal is selected as the electromagnetic ultrasonic guided wave signal to detect the defect in the main shaft. The T-mode guided wave signal is uniform circumferentially and propagates along an axial direction.

At act 502, a dispersion curve of the electromagnetic ultrasonic guided wave signal is drawn according to an outer diameter, an inner diameter and material characteristic of the main shaft.

At act 503, an operating point of the electromagnetic ultrasonic guided wave signal is selected, and a specific mode, an operating frequency and a wave speed of the electromagnetic ultrasonic guided wave signal are determined according to the dispersion curve.

For example, the T-mode guided wave signal is selected to detect the defect in the main shaft, which is uniform circumferentially and propagates along an axial direction. The outer diameter of the main shaft is 1.2 m, the inner diameter of the main shaft is 0.6 m, the material of the main shaft is structural steel, a longitudinal wave speed is 5940 ms, and a transverse wave speed is 3200 m/s. According to the drawn dispersion curve of the T-mode guided wave signal in the main shaft, there is only one guided wave signal of T (0, 1) mode in an operating frequency range of 5 kHz to 20 kHz, so that the corresponding guided wave signal propagating in the main shaft is pure, which is conducive to the defect detection of the main shaft. Therefore, T (0, 1) mode is selected for detecting the defect of the main shaft, the operating point frequency is selected as 15 kHz, and the wave speed of the guided wave signal with T (0, 1) mode is 3200 m/s and the wave length of the guided wave signal with T (0, 1) mode is about 0.21 m.

At act 504, a width, a length and a thickness of the nickel strap are calculated to be used in the device according to the operating point frequency and the wave speed of the guided wave signal; and the number of turns, a coil width, a cross-sectional area of the coil to be used in the device and a radial distance between the coil and the nickel strap are determined according to the operating point frequency and the wave speed of the guided wave signal.

For example, according to a principle that the coil width does not exceed a half of the wave length of the guided wave signal, a wire width is selected to be 0.1 m, and the number of turns is 100, and a cross-sectional area is 0.5 mm$^2$. Therefore, the nickel strap has a width of 0.11 m, a length of 3.75 m, and a thickness of 0.5 mm. The radial distance between the coil and the nickel strap is 5 mm.

At act 505, the nickel strap is magnetized in such a manner that a permanent magnet slides uniformly along a longitudinal direction of the nickel strap such that a residual magnetic field in the longitudinal direction is generated in the nickel strap. The sliding speed may be controlled in a range of 20 cm/s to 40 cm/s.

At act 506, epoxy resin glue is painted on an inner surface of the magnetized nickel strap uniformly and the magnetized nickel strap is stick on to the outer surface of the end of the main shaft circumferentially.

At act 507, the coil is mounted on an outer side of the magnetized nickel strap, in which a center of the coil coincides with a center of the nickel strap, and the coil and the magnetized nickel strap are disposed at the radial distance between each other.

At act 508, the signal collector and the wireless communication component are installed in the device.

The technical solutions provided by embodiments of the present disclosure have following advantageous effects.

As the wind turbine is far away from the ground, for example, some wind turbines are built on the ocean platform, there may be a long distance (a few kilometers to tens of kilometers) from the wind turbine to land. In the technical solutions of the present disclosure, the wireless transmission is employed to avoid the wire transmission in the long distance, thereby lowering cost.

In the technical solutions of the present disclosure, the wind turbine does not need to be shut down and the personnel do not need to carry the detection device into the wind turbine monitor room to detect the defect of the main shaft, thereby avoiding economic loss caused by shutting down the wind turbine.

In addition, the technical solutions of the present disclosure realize an efficient real-time on-line monitoring in the main shaft of the wind turbine.

Reference throughout this specification to "an embodiment," "some embodiments," "one embodiment", "another example," "an example," "a specific example," or "some examples," means that a particular feature, structure, material, or characteristic described in connection with the embodiment or example is included in at least one embodiment or example of the present disclosure. Thus, the appearances of the phrases such as "in some embodiments," "in one embodiment", "in an embodiment", "in another example," "in an example," "in a specific example," or "in some examples," in various places throughout this specification are not necessarily referring to the same embodiment or example of the present disclosure. Furthermore, the particular features, structures, materials, or characteristics may be combined in any suitable manner in one or more embodiments or examples.

Although explanatory embodiments have been shown and described, it would be appreciated by those skilled in the art that the above embodiments cannot be construed to limit the present disclosure, and changes, alternatives, and modifications can be made in the embodiments without departing from spirit, principles and scope of the present disclosure.

What is claimed is:

1. A device for detecting a defect in a main shaft of a wind turbine, comprising:
   an excitation source, configured to generate an electromagnetic ultrasonic guided wave signal;
   a nickel strap, magnetized and disposed on an outer surface of an end of the main shaft circumferentially;
   a coil, disposed at the nickel strap correspondingly and mounted on an outer side of the magnetized nickel strap, wherein a center of the coil coincides with a center of the nickel strap, the coil and the magnetized nickel strap are disposed at a radial distance between each other, the coil being configured to receive the electromagnetic ultrasonic guided wave signal such that the electromagnetic ultrasonic guided wave signal propagates in the main shaft, and the coil and the nickel strap are configured to transform the electromagnetic ultrasonic guided wave signal propagating in the main shaft into an electrical signal by electromagnetic induction;
   a signal collector, configured to collect the electrical signal and transform the electrical signal into guided wave detection data; and
   a wireless communication component, configured to transmit the guided wave detection data to a remote equipment, such that the defect is determined according to the guided wave detection data at the remote equipment.

2. The device according to claim 1, further comprising:
   a controller, configured to control the excitation source to generate the electromagnetic ultrasonic guided wave signal.

3. The device according to claim 1, further comprising:
   a storage, connected with the wireless communication component, and configured to receive and store the guided wave detection data.

4. The device according to claim 3, wherein the wireless communication component is further configured to transmit the guided wave detection data periodically.

5. The device according to claim 1, wherein the electromagnetic ultrasonic guided wave signal is a periodic pulse square wave signal.

6. The device according to claim 1, further comprising:
   a matching and coupling component, configured to receive the electromagnetic ultrasonic guided wave signal, and match and couple the electromagnetic ultrasonic guided wave signal, and transmit the electromagnetic ultrasonic guided wave signal after matching and coupling to the coil.

7. The device according to claim 6, wherein the matching and coupling component is further configured to receive the electrical signal, and match and couple the electrical signal, and transmit the electrical signal after matching and coupling to the signal collector.

8. The device according to claim 1, wherein a length of the nickel strap is less than a circumference of the outer surface of the end of the main shaft by a preset value.

9. The device according to claim 1, wherein the nickel strap is magnetized in such a manner that a permanent magnet slides uniformly along a longitudinal direction of the nickel strap such that a residual magnetic field in the longitudinal direction is generated in the nickel strap.

10. The device according to claim 1, wherein a center of the coil coincides with a center of the nickel strap.

11. The device according to claim 1, wherein an inner surface of the nickel strap is painted with epoxy resin glue.

12. The device according to claim 1, wherein the electromagnetic ultrasonic guided wave signal has a T-mode, which is uniform circumferentially and propagates along an axial direction.

13. A method for detecting a defect in a main shaft of a wind turbine, wherein a nickel strap is magnetized and disposed on an outer surface of an end of the main shaft, a coil is disposed at the nickel strap correspondingly and mounted on an outer side of the magnetized nickel strap, a center of the coil coincides with a center of the nickel strap, the coil and the magnetized nickel strap being disposed at a radial distance between each other, and the method comprises:

generating, by an excitation source, an electromagnetic ultrasonic guided wave signal;

receiving, by the coil, the electromagnetic ultrasonic guided wave signal, such that the electromagnetic ultrasonic guided wave signal propagates in the main shaft;

transforming, by the coil and the nickel strap, the electromagnetic ultrasonic guided wave signal propagating in the main shaft into an electrical signal;

transforming the electrical signal into guided wave detection data; and transmitting the guided wave detection data to a remote equipment, such that the defect is determined according to the guided wave detection data at the remote equipment.

14. The method according to claim 13, wherein the electromagnetic ultrasonic guided wave signal is a periodic pulse square wave signal.

15. The method according to claim 13, wherein the electromagnetic ultrasonic guided wave signal has a T-mode, which is uniform circumferentially and propagates along an axial direction.

16. A method for manufacturing a device for detecting a defect in a main shaft of a wind turbine, comprising:

determining an electromagnetic ultrasonic guided wave signal to be generated by an excitation source installed in the device;

drawing a dispersion curve of the electromagnetic ultrasonic guided wave signal according to an outer diameter, an inner diameter and material characteristic of the main shaft;

selecting an operating point of the electromagnetic ultrasonic guided wave signal and determining an operating frequency and a wave speed of the electromagnetic ultrasonic guided wave signal according to the dispersion curve;

calculating a width, a length, and a thickness of a nickel strap to be used in the device according to the operating frequency and the wave speed;

determining a number of turns, a width and a cross sectional area of a coil to be used in the device, and a radial distance between the coil and the nickel strap according to the operating point frequency and the wave speed of the guided wave signal;

magnetizing the nickel strap by sliding a permanent magnet uniformly along a longitudinal direction of the nickel strap, such that a residual magnetic field in the longitudinal direction is generated in the nickel strap;

painting epoxy resin glue on an inner surface of the nickel strap;

sticking the nickel strap magnetized on to an outer surface of an end of the main shaft circumferentially;

installing the coil on an outer side of the nickel strap magnetized to enable a center of the coil to coincide with a center of the nickel strap magnetized and to enable the coil to distance from nickel strap magnetized the radial distance; and installing the signal collector and the wireless communication component in the device.

17. The method according to claim 16, wherein the length of the nickel strap is less than a circumference of the outer surface of the end of the main shaft by a preset value.

* * * * *